(12) United States Patent
Ebeid

(10) Patent No.: US 11,559,667 B2
(45) Date of Patent: Jan. 24, 2023

(54) GUIDEWIRE RETAINING ACCESSORY

(71) Applicant: Makram R. Ebeid, Ridgeland, MS (US)

(72) Inventor: Makram R. Ebeid, Ridgeland, MS (US)

(*) Notice: Subject to any disclaimer, the term of this patent is extended or adjusted under 35 U.S.C. 154(b) by 982 days.

(21) Appl. No.: 16/356,436

(22) Filed: Mar. 18, 2019

(65) Prior Publication Data

US 2020/0297978 A1    Sep. 24, 2020

(51) Int. Cl.
*A61M 25/09* (2006.01)
*A61M 39/10* (2006.01)
*A61M 39/22* (2006.01)
*A61M 25/00* (2006.01)

(52) U.S. Cl.
CPC ............ *A61M 25/09* (2013.01); *A61M 39/10* (2013.01); *A61M 39/223* (2013.01); *A61M 2025/0019* (2013.01); *A61M 2025/09108* (2013.01); *A61M 2025/09125* (2013.01); *A61M 2039/229* (2013.01)

(58) Field of Classification Search
CPC ................ A61M 25/09; A61M 25/002; A61M 2025/0019; A61M 2025/09108; A61M 2025/09125; A61M 39/10; A61M 39/223; A61M 2039/229
See application file for complete search history.

(56) References Cited

U.S. PATENT DOCUMENTS

| | | | |
|---|---|---|---|
| 4,270,535 A | 6/1981 | Bogue et al. | |
| 4,903,826 A | 2/1990 | Pearce | |
| 5,125,416 A | 6/1992 | Phillips | |
| 5,125,904 A | 6/1992 | Lee | |
| 5,133,364 A | 7/1992 | Palermo et al. | |
| 5,250,038 A | 10/1993 | Melker et al. | |
| 5,279,573 A | 1/1994 | Klosterman | |
| 5,282,478 A | 2/1994 | Fleischhaker, Jr. et al. | |
| 5,308,322 A * | 5/1994 | Tennican | A61M 39/223 604/83 |
| 5,312,355 A | 5/1994 | Lee | |
| 5,358,495 A | 10/1994 | Lynn | |
| 5,364,355 A | 11/1994 | Alden et al. | |
| 5,443,081 A | 8/1995 | Klosterman | |

(Continued)

FOREIGN PATENT DOCUMENTS

| | | |
|---|---|---|
| WO | WO 93/08730 | 5/1993 |
| WO | WO 2004/022433 A2 | 3/2004 |
| WO | WO 2016/196785 A1 | 12/2016 |

OTHER PUBLICATIONS

European Search Report for EP 20 161 440.1; dated Aug. 14, 2020; 9 pages.

*Primary Examiner* — Tasnim Mehjabin Ahmed

(74) *Attorney, Agent, or Firm* — Barclay Damon LLP

(57) ABSTRACT

A guidewire support accessory includes one or more hollow tubular sections, each of the hollow tubular sections including a first end and an opposing second end for individually supporting a plurality of medical guidewires. A connector is disposed at the first end. Each of the one or more hollow tubular sections is sized and configured to receive a medical guidewire maintained in a coiled arrangement. The accessory includes at least one clamp configured to releasably retain a guidewire in the coiled arrangement, as well as at least one wiping or cleaning feature.

17 Claims, 14 Drawing Sheets

(56) References Cited

U.S. PATENT DOCUMENTS

| | | |
|---|---|---|
| 5,568,865 A | 10/1996 | Mase et al. |
| 5,634,475 A | 6/1997 | Wolvek |
| 5,666,968 A | 9/1997 | Imran et al. |
| 5,730,150 A | 3/1998 | Peppel et al. |
| 5,738,213 A | 4/1998 | Whiting et al. |
| 5,800,384 A | 9/1998 | Russell et al. |
| 5,843,002 A | 12/1998 | Pecor et al. |
| 6,022,319 A | 2/2000 | Willard et al. |
| 6,139,540 A | 10/2000 | Rost et al. |
| 6,231,564 B1 | 5/2001 | Gambale |
| 6,309,379 B1 | 10/2001 | Willard et al. |
| 6,375,006 B1 | 4/2002 | Samuels |
| 6,482,171 B1 | 10/2002 | Toman et al. |
| 6,508,790 B1 | 1/2003 | Lawrence |
| 6,547,072 B2 | 4/2003 | Whiting et al. |
| 6,569,106 B1 * | 5/2003 | Ullman ............... A61M 25/09 600/585 |
| 6,588,588 B2 | 7/2003 | Samuels |
| 6,802,323 B1 | 10/2004 | Truwit et al. |
| 6,827,710 B1 | 12/2004 | Mooney et al. |
| 7,204,464 B2 | 4/2007 | Chandra et al. |
| 7,334,678 B2 | 2/2008 | Kesler et al. |
| 8,567,657 B2 | 10/2013 | Andreychuk |
| 8,617,231 B2 | 12/2013 | Vardi et al. |
| 8,961,452 B2 | 2/2015 | Purdy |
| 9,101,736 B2 | 8/2015 | Qureshi |
| 9,162,038 B2 | 10/2015 | Rottenberg et al. |
| 2002/0072712 A1 | 6/2002 | Nool et al. |
| 2004/0064086 A1 | 4/2004 | Gottlieb et al. |
| 2004/0068248 A1 | 4/2004 | Mooney et al. |
| 2008/0007045 A1 * | 1/2008 | Steppe ............... A61M 39/10 285/133.11 |
| 2009/0234290 A1 | 9/2009 | Fisher et al. |
| 2012/0022470 A1 * | 1/2012 | Kuniyasu ............ A61M 25/002 604/265 |
| 2015/0094693 A1 * | 4/2015 | Suzuki ............... A61M 25/002 604/528 |

* cited by examiner

GUIDEWIRE RETAINING ACCESSORY

TECHNICAL FIELD

This application is directed to the field of cardiac catheterization or interventional radiological procedures, and more specifically to an accessory external to the body of a patient that supports and maintains one or more medical guidewires for ready use during catheter or radiological procedures.

BACKGROUND

The number of surgical procedures is ever increasing. With this growing number, an equal demand and preference has been made for performing interventional procedures as opposed to open heart/chest procedures. To that end, it is estimated that more than 3.5 million catheterization or interventional procedures are performed in the United States yearly. The conduction of interventional/special procedures requires the use of guidewires, which are thin, flexible sections of a medical grade wire that is inserted into the body. A guidewire is designed to guide a larger instrument such as a catheter, feeding tube, and central venous tube, among others, for delivery to an intended medical site. For example, guidewires are commonly used for placement of balloon dilatation catheters during percutaneous transluminal coronary angioplasty (PTCA), placing percutaneous valves as transcatheter aortic valve replacement (TAVR), percutaneous transcatheter pulmonary valve replacement (TPVR), stenting, among a plethora of other related procedures.

Additionally, there are several metrics of performance for which guidewires possess varying ability wherein several guidewires may be required during a single catheter or radiological procedure. Each of the these metrics depend on the materials, as well as certain design attributes of the guidewire. More specifically, key metrics used for selecting a guidewire(s) include trackability, torqueability, flexibility, crossability, opacity and supportability. Trackability has been defined as the ability of the guidewire to follow the soft floppy tip into a vessel, and especially through curves of tortuous vessels. For example, less stiff, floppy guidewires can navigate sharp bends much easier than stiff guidewires. Trackability is affected by how the tip of the guidewire is designed, as well as the material comprising the core wire. Torqueability is the ability of the guidewire to apply rotational force at the proximal end of the guidewire and have that rotational force transmitted in order to maintain the proper amount of control at the distal (tip) end. Flexibility is the ability of the guidewire to flex on its longitudinal axis while maintaining torque and trackability. This metric is important, for example, when reaching a tortuous lesion. The core of guidewires can be made from a very flexible material (i.e., nitinol) or a much stiffer material (i.e., stainless steel), which dictates the guidewire's flexibility. Opacity refers to the ability of the guidewire to track radiometric or other forms of markers. Crossability refers to the ability of the guidewire to cross a lesion with little or no resistance. In this regard, stiffer guidewires can usually cross significant lesions. Finally, supportability is the ability of the guidewire to support the passage of another device (e.g., catheter, etc.) or system over the guidewire. To achieve any or a portion of the above performance metrics, guidewires may include a number of additional structural features. For example, certain guidewires may include tapers, angles, and arcs to aid in maneuverability.

In terms of overall design, guidewires are usually made from one of two (2) basic configurations; namely, solid steel or nitinol core guidewires or solid core guidewires wrapped in a smaller wire coil or braid. Coiled or braided guidewires offer a large amount of flexibility, pushability and kink resistance. Some known guidewires employ a nitinol tube with micro-cut slots instead of braided wire to improve torque control.

Nitinol wire, used alone or braided with stainless steel, helps increase flexibility and allows the guidewire to spring back into shape after navigating a tortuous vessel. Most guide wires have a floppy tip and a stiff body to enable easy tip navigation, with good pushability being offered by the stiffer section of the guidewire. The tips may be straight or may assume a J-shape or other angle. The range of wire diameters required during a catheter or radiological procedure varies considerably for a plurality of guidewires that could be used or should be available to the physician. Most known guidewires have diameters in the range of about 0.014-0.038 inches and lengths of about 80-450 cm.

Therefore and given the different attributes, it is common for multiple guidewires to be used, some repeatably during the conduction of cardiac catheterization, radiological or other interventional procedures, and depending, for example, on the complexity of the procedure. Usually a guidewire is removed from its package and inserted in the patient during the procedure in order to reach a certain area. Once the guidewire has reached the area, the guidewire is removed from the patient and set aside to be used again, if needed, during the procedure. Typically and when a guidewire is removed from the body of the patient, an assistant may loop the guidewire and put the guidewire into a knot so that the guidewire does not unloop and fall from the table onto the floor or other nonsterile surface. In other instances, a wet towel may be placed onto the looped guidewire.

When the physician or operator needs the guidewire again, the assistant tries to provide the guidewire as quickly as possible. Frequently, a guidewire may be needed instantaneously especially during critical parts of the procedure. Sometimes, the formed knot gets too tight, which delays the availability of the guidewire or kinks the guidewire, rendering the guidewire useless for its intended purpose. In other instances and if the wet towel is not removed carefully, the guidewire may unloop very quickly and become difficult to handle or the guidewire may slip from the table onto the floor. In addition, the guidewires should be wiped frequently to avoid the presence of any blood clots on the guidewire before reintroducing the guidewire to a surgical site. It is also preferable to wet the guidewire to ease advancement of the guidewire into the patient. The latter wetting is especially important in that some guidewires may include a suitable hydrophilic coating in order to reduce friction and assist in movement of the guidewire to an intended medical site or area.

The handling of guidewires in general, once the guidewire is removed from its package and for purposes of use or reuse, is not easy. This difficulty can significantly delay the ability to have a specific guidewire available and can therefore mean the difference between success and failure in the procedure. Recognition of this long felt and unresolved need cannot be over emphasized. In the handling of even a single guidewire, there are risks in which a guidewire may become kinked or fall on the floor. These risks become even greater in dealing with a plurality of guidewires, as is common during an invasive medical procedure. There is a further risk that individuals may be inadvertently hit by a dirty guidewire during rapid wire un-looping.

Accordingly, there is a pervasive and general need in the field to be able to access and readily use at least one or a plurality of guidewires during the course of a surgical procedure without delays or risks that affect time or efficiency. In addition and often a specific guidewire(s) must be counted upon for use a multiple number of times during the invasive procedure. Therefore, a related need exists to reliably retain guidewires to enable multiple uses of same in an interventional environment and to permit easy access to the guidewires for any number of uses.

BRIEF DESCRIPTION

Therefore and according to one aspect, there is provided a guidewire support accessory comprising one or more hollow tubular sections formed and maintained in a coiled arrangement, the one or more hollow tube sections including a first open end and a second open end. Each hollow tubular section is configured to receive a medical guidewire. Clamp means are provided for releasably retaining the guidewire within the accessory while in the coiled configuration. According to one version, the clamp means can include a Y—connector having a rotary or other form of integrated rotary valve, such as a hemostatic valve. According to another version, one or more clamps can be provided at intermediate axial portions of the hollow tubular sections, the clamp(s) being sized and configured to apply pressure and retain a guidewire within the hollow tubular section(s) in the coiled configuration.

In at least one embodiment, a sponge, gauze or other cleaning means is disposed within each one or more hollow tubing section adjacent one end thereof through which the guidewire passes when either storing within and/or releasing the guidewire from the support accessory. In at least one version, at least one hollow tubular section includes a side arm connector that is disposed intermediately between the first and second open ends. In another version, at least one hollow tubular section can include an access opening formed in an intermediate portion of the length of the tube section to enable a tool to engage the stiffer portion of a retained guidewire to permit the guidewire to be easily and reliably deployed for use.

According to another aspect, there is described a method for retaining and maintaining one or more medical guidewires during a medical/interventional procedure. The method includes the steps of individually retaining one or more guidewires in a coiled hollow section of medical grade tubing, each coiled section of tubing including a first end and a second opposing end that is formed in a coiled configuration, fixedly retaining the guidewire within the hollow tubular section, and selectively releasing a guidewire from one of the one or more individual hollow tubular sections, as needed, during an interventional procedure. According to at least one version, a rotary valve or other clamping means can be used to retain the guidewire within the accessory.

The method further includes providing cleaning/wiping means for a guidewire that is retained in the accessory or replacing the guidewire within the accessory. According to one version, a sponge, gauze or other wiping/cleaning member is maintained within the accessory through which the guidewire passes when either retaining or removing the guidewire. In one version, the wiping/cleaning means is disposed within the connector. The wiping material can be made wet by flushing the material using a side arm connector of the accessory, thereby cleaning the guidewire and providing wetness to hydrophilic coated guidewires. The one or more hollow tubular sections can be color coded or similarly marked in order to better identify the guidewire that is retained.

According to yet another aspect, there is provided a method for manufacturing a guidewire retaining accessory, comprising the steps of providing one or more hollow tubular sections, each tubular section having a first end and an opposing second end. A connector is attached to the first end of each hollow tubular section and a clamp is provided to retain a guidewire within the one or more hollow tubular sections. According to this method, a wiping or cleaning member is further provided within the accessory.

The herein described guidewire support accessory is intended to expedite and facilitate wire handling while individually protecting one or a plurality of medical guidewires, as well as individually wiping each guidewire and keeping the guidewire(s) moist during diagnostic and interventional cardiac catheterization and radiological procedures, especially during complex procedures requiring multiple and fragile wires which should not be kinked allowing rapid handling of the wires. The herein described accessory/sheath design allows easy guidewire exchanges thereby saving valuable time during the procedure, as well as protecting the guidewire form from becoming kinked or damaged, and preserving wire form integrity or preventing the wire from falling on the floor. The herein described guidewire support accessory is designed to alleviate these problems.

The herein described accessory is external to and therefore does not enter the patient's body. The herein described accessory permits the storage of one or a plurality of guidewires in a coiled arrangement for use as needed in a medical/interventional procedure.

A number of advantages are realized using the herein described retaining accessory. First, the herein described accessory maintains the looping of one or preferably a plurality of guidewires, individually keeping each of the retained guidewires contained and coiled until any of the guidewires are actually needed.

The design of the herein described accessory also enables rapid, easy access to each retained guidewire to the physician or operator while the guidewire is being unlooped.

In addition, the herein described supporting accessory is configured to individually wipe the stored guidewires during looping and inserting of same into the accessory, as well as when the guidewire(s) are being removed from the accessory.

In addition, the design of the herein described accessory permits ease of flushing the guidewire during insertion into the accessory, while each guidewire is retained in the accessory, or during removal from the accessory; which of special importance, especially for hydrophilically coated guidewires.

The herein described accessory includes a mechanism to access the stiff part of any or all retained guidewires, if needed, to avoid handling of the floppy proximal fragile end of the guidewire. Means are provided in at least one version for accessing the stiff intermediate portions of the guidewire or the stiff end of shorter guidewires.

In addition, the herein described accessory includes at least one mechanism to stabilize each retained guidewire inside the coiled loop. This latter feature avoids inadvertently pushing the guidewire inside the loop and making it more difficult to rapidly access the guidewire.

According to at least one version, a hollow tube can be inserted into an intermediate access port of the accessory, allowing the stiff end of the guidewire to exit the accessory from the access port and permitting access to the stiff end of shorter guidewires, if needed.

Advantageously, the herein described accessory will permit the handling and retention of guidewires of varying lengths while permitting the operator to access the stiff portions of the retained guidewire, as needed.

These and other features and advantages will be readily apparent from the following Detailed Description, which should be read in conjunction with the accompanying drawings.

DETAILED DESCRIPTION

The following description relates to certain exemplary embodiments of a guidewire retaining or supporting accessory, each embodiment incorporating a number of inventive aspects. More specifically, the herein described accessory is configured to individually retain one or more medical guidewires for repeated use, as needed, during a catheterization, radiological or other interventional procedure. While the herein described embodiments may be specific to the retention of a predetermined number (three (3)) of medical guidewires, it will be readily apparent from this description that the number of guidewires that can be effectively retained by the accessory can be easily varied to one or more. In addition and throughout the course of discussion, a number of terms are used to provide a suitable frame of reference for the accompanying drawings. These terms, which include "distal", "proximal", "inner", "outer", "first", "second", among others, are not intended to be overlimiting of the scope of the invention, unless so specifically indicated. It will be further evident that a number of variations and modifications are possible that embody the inventive aspects described herein, and as will be apparent from the following description.

Figure 1:
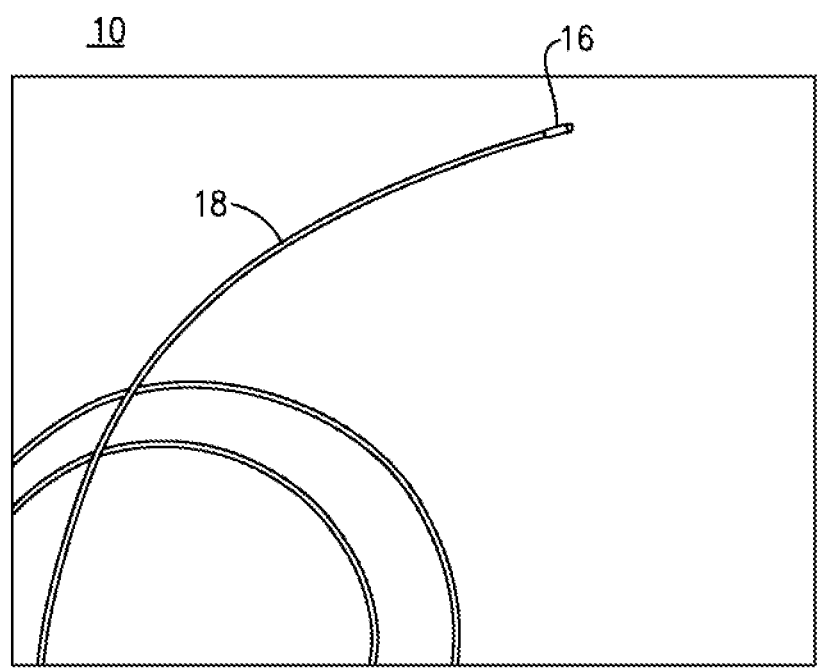
FIG. 1 is a schematic view of a typical medical guidewire.

With reference to FIG. 1, there is first shown for background purposes a medical guidewire 10 used for various surgical procedures. The guidewire 10 is typically made from a highly flexible material, such as Nitonel although other stiffer materials, such as stainless steel can be utilized depending for example on the design attributes (torqueability, flexibility, pushability, opacity, etc) and the function of the guidewire in a medical (catheterization or other interventional) procedure. Each guidewire 10 commonly includes a first end and an opposing second end. The first or distal end of the guidewire 10 includes a floppy soft tip 16 with a proximally extending and stiffer intermediate and proximal portion of the guidewire 10. The guidewire 10 is further defined by a core 18 that extends over substantially the length of the guidewire 10. Though not shown, the guidewire 10 can be configured with other features such as tapers, arcs and the like, depending on the application/procedure.

Figure 2:
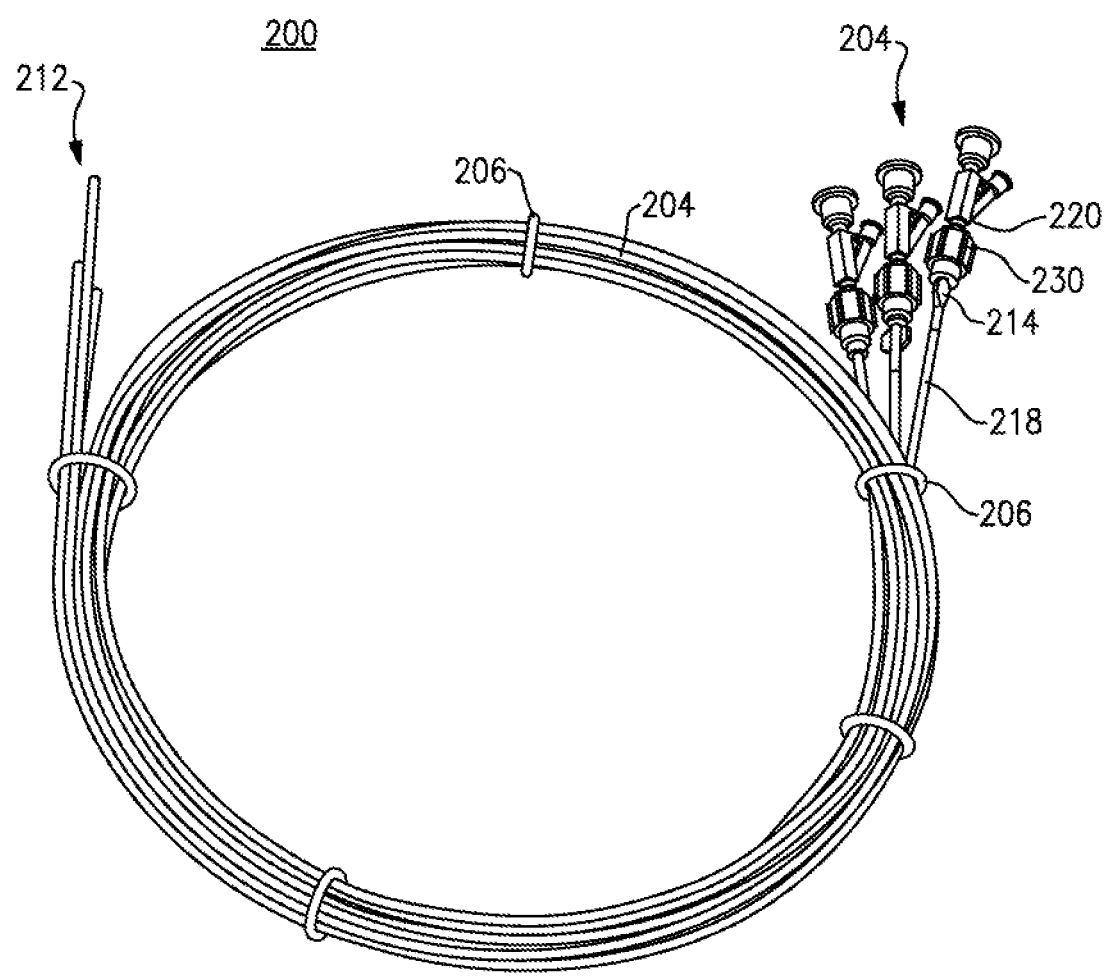
FIG. 2 is a perspective view of a guidewire supporting accessory in accordance with an exemplary embodiment of the invention.
Figure 3:
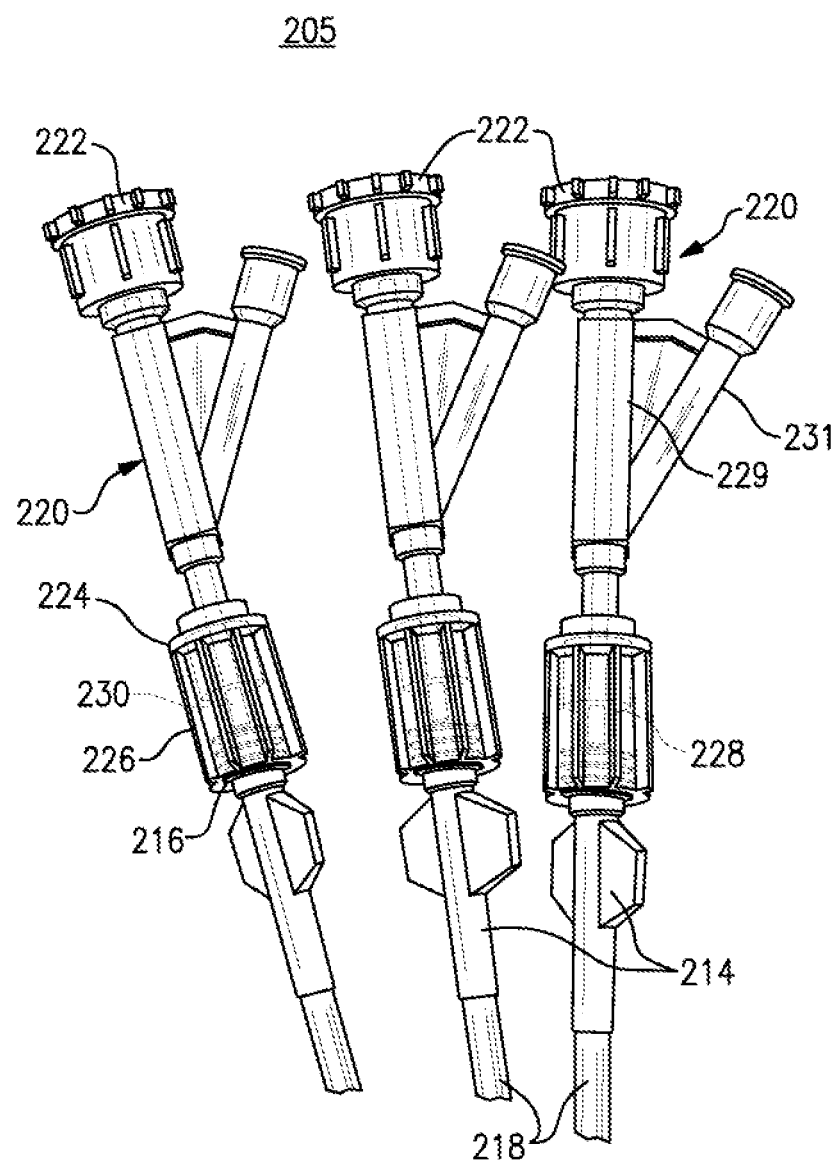
FIG. 3 is a perspective view of one end of the guidewire supporting accessory of FIG. 2.
Figure 4:
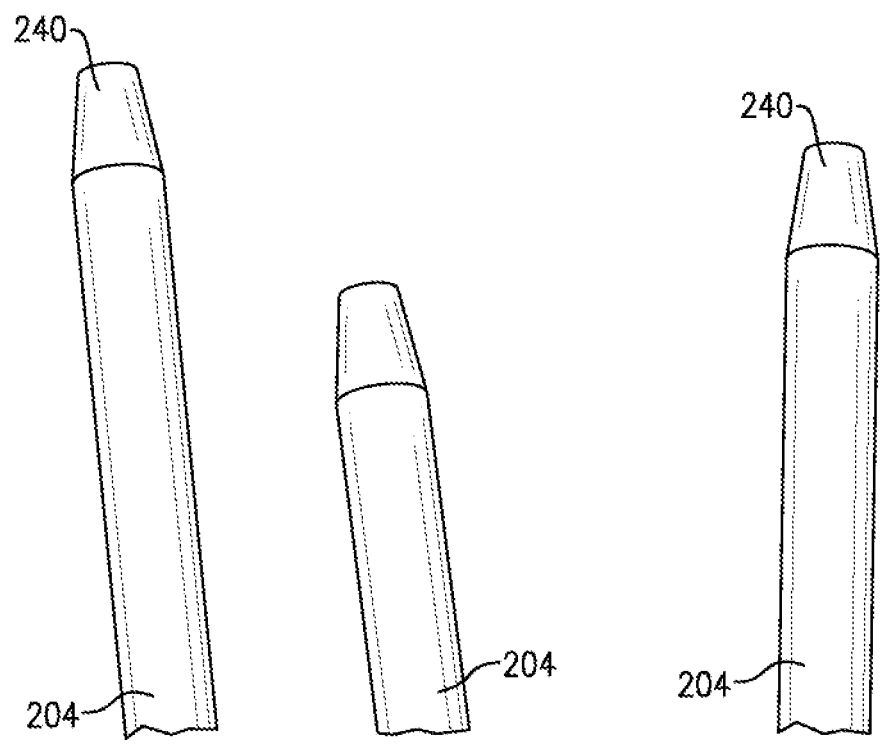
FIG. 4 is a perspective view of the other end of the guidewire supporting accessory of FIGS. 2 and 3.

With reference to FIGS. 2-4, there is provided a multiple guidewire retaining or supporting accessory 200 in accordance with a first embodiment in which the guidewire retaining accessory 200 is designed to individually retain a predetermined number of medical guidewires. According to this specific embodiment, the accessory 200 is configured to retain three (3) guidewires, such as those shown in FIG. 1, and includes three (3) sections of hollow plastic tubing 204 that are coiled into a loop of an appropriate diameter. In this embodiment, each of the hollow tubular sections 204 has a predetermined length of about 300 cm and a coiled diameter of about 25 cm, though these dimensions are only intended to be representative and can be easily varied. The hollow tubular sections 204 are retained in the coiled arrangement using a series of clip members 206, each suitably positioned in spaced relation along the length of the coiled tubular sections 204. Five (5) clip members are provided in the supporting accessory 200 according to the presently described embodiment, although this number can be suitably varied.

Each of the hollow tubular sections 204 is defined by a first end 205 and an opposing second end 212. A luer hub 214 is attached to a first end 205 of each hollow tubing section 204, which according to this embodiment is a male luer lug having a threaded portion 216 at an extending end. The opposite end of each luer hub 214 is secured to the first end 205 of the hollow tubular section 204 using a section of connector hose or tubing 218. A Y-connector 220 includes a screw cap 222 at its port end, as well as a contained Tuohy adapter 224 and a female luer connector 226 at its opposite connecting end, the latter enabling attachment of the connector to the threaded portion 216 of the male luer hub 214. The Y-connector 220 according to this embodiment further includes a hollow main port 229 extending through the connector 220, as well as an integrated rotary valve 228, and more specifically a rotary hemostasis valve in addition to an extending side port 231, forming the Y configuration of the connector 220. The interior of the Y-connector 220 according to this version further retains at least one wiping or cleaning member (not shown) designed to clean the guidewire as the guidewire enters the accessory 200 or while the guidewire is being removed from the accessory 200. According to this embodiment, the wiping or cleaning member can be a sponge ring that is disposed within the interior of the Y-connector 220. More specifically and in terms of assembly, the screw cap 222 and the gasket of the Tuohy adapter 224 of the Y-connector 220 are removed and the sponge ring is placed within the hollow interior of the Y-connector 220. The gasket and the screw cap 222 are then reassembled into place. Alternatively and in lieu of a sponge, a section of gauze or similar wiping or cleaning material can be disposed on a fitted mandrel (not shown) and disposed within the main port 329 of the connector 320.

The rotary valve 228 can be tightened in a known manner by external rotation to lock a retained guidewire in place. As described in a later embodiment and in lieu of the rotary valve 228, other means can be utilized for retaining a guidewire within the hollow tubular section 204. Each of the luer hubs 214 or at least portions of each hollow tubular section 204 can be color-coded in order to more readily identify a guidewire being stored by the herein described accessory 200.

As shown in FIG. 4, the opposite second end 212 of each of the hollow tubular sections 204 are defined by tapered ends 240 to optionally assist in facilitating flushing in order to prevent liquid from leaking too easily from the accessory 200. Alternatively, an elastic (e.g., rubber or latex) type of outlet (not shown) could be provided on the second end 212 to keep the flushing fluid within the accessory with minimal leakage while the guidewire is extruded from the first end. Other connector configurations can be provided at the second end 212, such as a luer hub (not shown).

In use, a guidewire is removed from its original packaging for insertion into the body of the patient and the original packaging is discarded. Following use during the surgical procedure, the guidewire is inserted into the retaining accessory 200 after the guidewire is pulled from the body of the patient (not shown). The guidewire is inserted into the first end 205 of the accessory 200 and more specifically the connector 220 by pushing the stiff end of the guidewire, which is typically outside of the body of the patient into the main port 229. The guidewire can be flushed via the side port 231 of the connector 220 and cleaned by the contained wiping member 230 through which the guidewire passes.

Removal of the guidewire from the accessory 200 can occur in different ways. In a first version, the soft tip end of the guidewire, which is outside of the accessory 200, can be carefully pulled to enable extraction of the retained guidewire from the coiled tubular section 204 through the connector 220. Alternatively, a small break or access opening (not shown) can be provided in an intermediate portion of the hollow tubular section 204 to permit the passage of a small tool (not shown) to contact the stiff middle part of the retained guidewire in order to push the guidewire from the accessory 200 through the first end 205. Alternatively, each of the hollow tubular sections 204 can include an intermediate break (not shown), enabling the insertion of a smaller diameter tube that is configured and shaped to access and engage against the stiffer portion of shorter guidewires. According to yet another version and depending on the length of the hollow tubular sections 204, a proximal end portion of the guidewire may extend from the tapered ends 240 of the second end 212 of the accessory 200, enabling the guidewire to be pushed through and released from the supporting accessory 200, as needed.

As discussed, the foregoing supporting apparatus can be offered in shorter versions to be used for retaining shorter guidewires. The accessory 200 can also be provided with 1 or 2 hollow tubular sections to handle one or 2 wires or more than 3 hollow tubular sections to handle a larger corresponding number of medical guidewires.

With reference to FIGS. 5-10, there is shown a second exemplary embodiment of a guidewire retaining accessory 300. The retaining accessory 300 according to this embodiment is defined by a plurality of hollow tubular sections 304, preferably made from a medical grade plastic that are formed into a coiled arrangement. As in the preceding embodiment, any suitable number of hollow tubular sections 304 can be used, but for purposes of this embodiment three (3) tubular sections 304 are provided. A plurality of clip members 306 are disposed in spaced relation along the coiled arrangement in order to maintain the plurality of hollow tubular sections 304 in the coiled arrangement. The clip members 306 can be of any appropriate design that acts to couple the tubular sections 304 together and retain the coupled tubular sections 304 in the defined coiled shape. According to this specific embodiment, each hollow tubular section 304 has an internal diameter of approximately 0.052 inches to accommodate larger guidewires with minimal amounts of friction. In addition, the tubular sections are further defined by a predetermined length of about 265 cm, creating a coiled diameter of about 25 cm, although each of these specific parameters can be suitably varied to accommodate specific guidewires.

Figure 5:
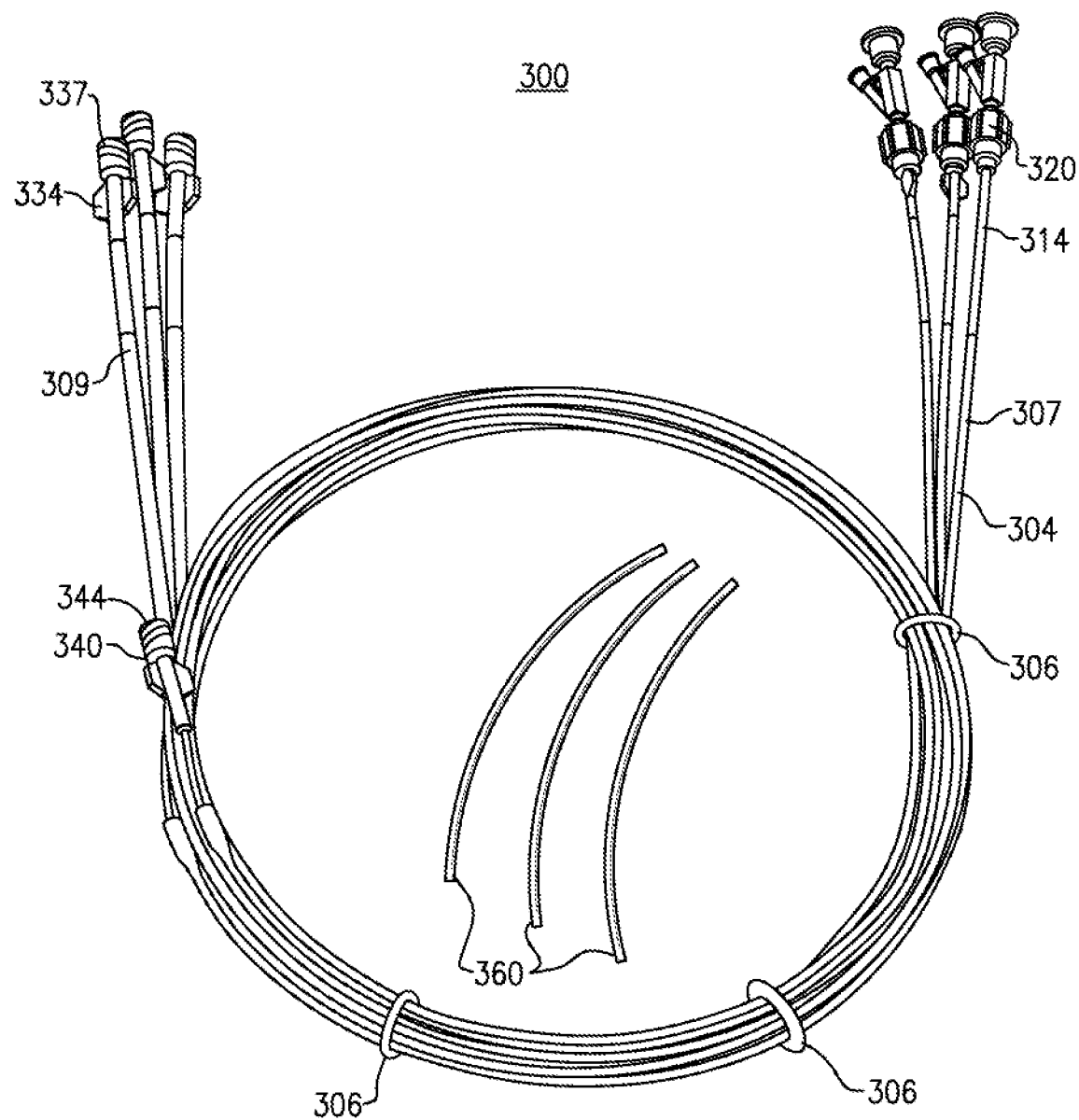
FIG. 5 is a perspective view of a guidewire supporting accessory in accordance with another exemplary embodiment.
Figure 6:
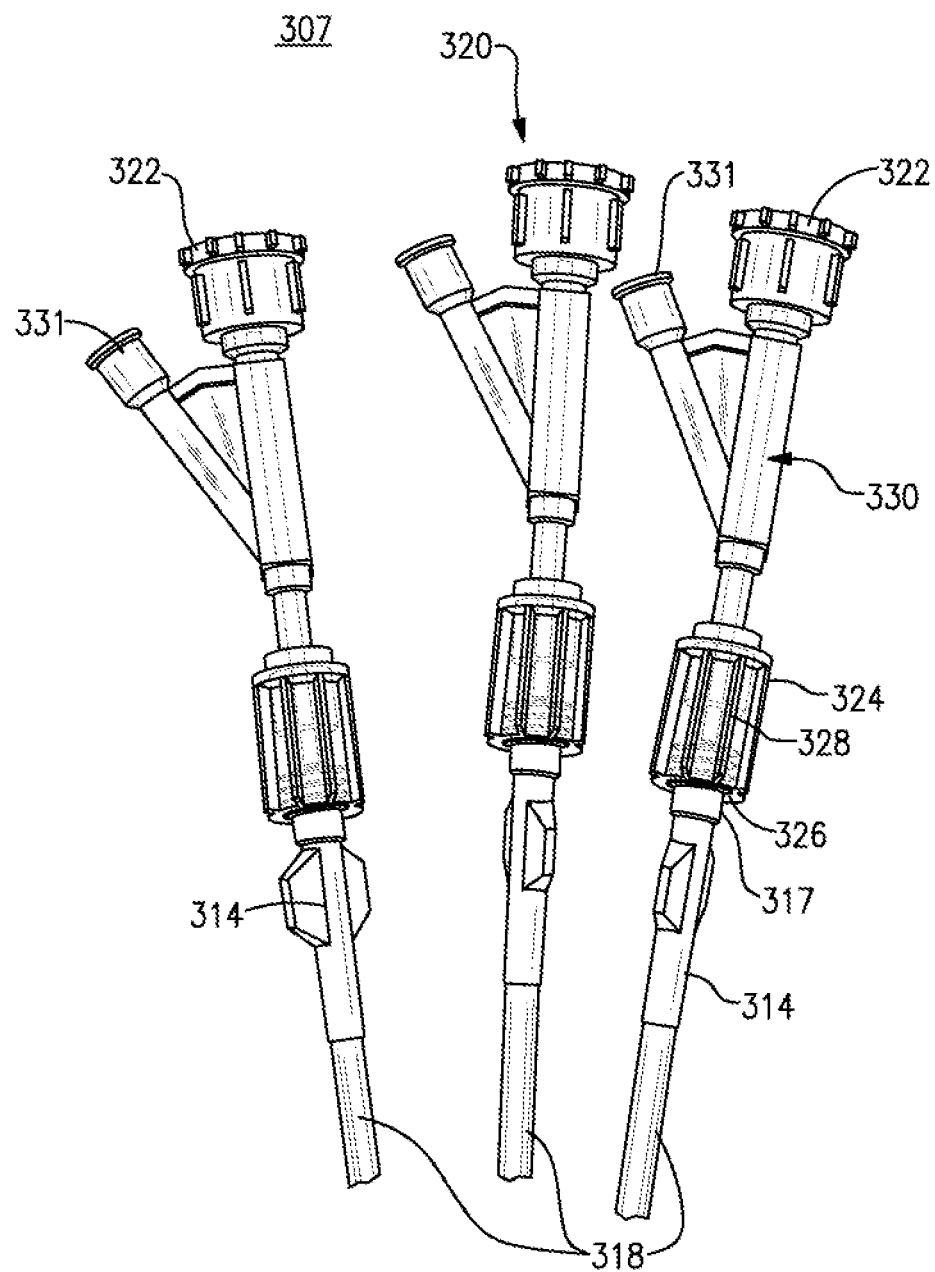
FIG. 6 is a perspective view of one end of the guidewire supporting accessory of FIG. 5.

Each hollow tubular section 304 of the herein described retaining accessory 300 is defined by a first end 307 and an opposing second end 309. As shown in FIGS. 5 and 6, the first end 307 includes a first luer hub 314 having a plurality of external threads disposed on a connecting end as part of a threaded portion 317. The first luer hub 314 is attached at an opposing end to a short section of a connecting hose or tubing 318 to the first end 307 of the hollow tubular section 304. According to this embodiment, the connecting hose 318 has a length of about 0.140 inches and a diameter of about 0.097 inches.

A Y-connector 320 is attached to the threaded portion 317 of the first luer hub 314 and more specifically to a female luer connector 326 formed at one end of the Y-connector 320. The Y-connector 320 further includes a screw cap 322 at an opposite end of the connector 320, as well as a contained Tuohy adapter 324 and an integrated rotary valve 328, such as a rotary hemostasis valve. The Y-connector 320 is defined by a hollow interior defined by a main port 329, as well as an integrated side port 331, which combine to form the Y shaped connection. In addition and according to this embodiment, the Y-connector 320 retains a wiping or cleaning member 330 through which a supported guidewire passes.

The wiping or cleaning member 330 is used to wipe the guidewire and moisten the wire during insertion of the wire into the accessory 300 and when removing the guidewire from the accessory 300. More specifically, the guidewire passes through the center of the wiping member 330 (e.g., sponge (or gauze)). The wiping member 330 does not create friction and also wipes the guidewire adequately. Any material that can be moistened and can wipe the guidewire can be utilized as a wiping or cleaning member. In this embodiment, the screw cap 322 and the gasket at the front end of the Tuohy adapter 324 of the connector 320 are removed. A section of wiping or cleaning material is wrapped around a mandrel and passed through the Tuohy adapter 324. Adhesive is applied to each end of the wiping material to hold the wiping material in place. The length of the wiping member 330 according to this embodiment is about 6 cm, but it will be understood to those of sufficient skill that this parameter can be suitably varied. Other suitable cleaning or wiping features can alternatively be provided. For example, a sponge disposed in a ring-like configuration (not shown) can be disposed within the connector 320 and configured to allow a guidewire to pass therethrough. Alternatively, the cleaning or wiping member 330 can be otherwise disposed within the confines of the supporting accessory 300 anywhere through which the guidewire passes.

Once a guidewire is disposed within the accessory 300, the rotary valve 328 can be engaged sufficiently by external rotation to retain a guidewire, the latter having a smaller diameter than the diameter of the hollow tubing section 304. Once retained, the rotary valve 328 at the front end of the herein described accessory 300 on the connector 320 will allow the entry point to become smaller to stabilize the smaller guidewires that it does not inadvertently move. The accessory 300 allows a retained guidewire to be flushed, cleaned and moistened as well as ready to be reinserted, as needed, during the interventional procedure.

Figure 7:
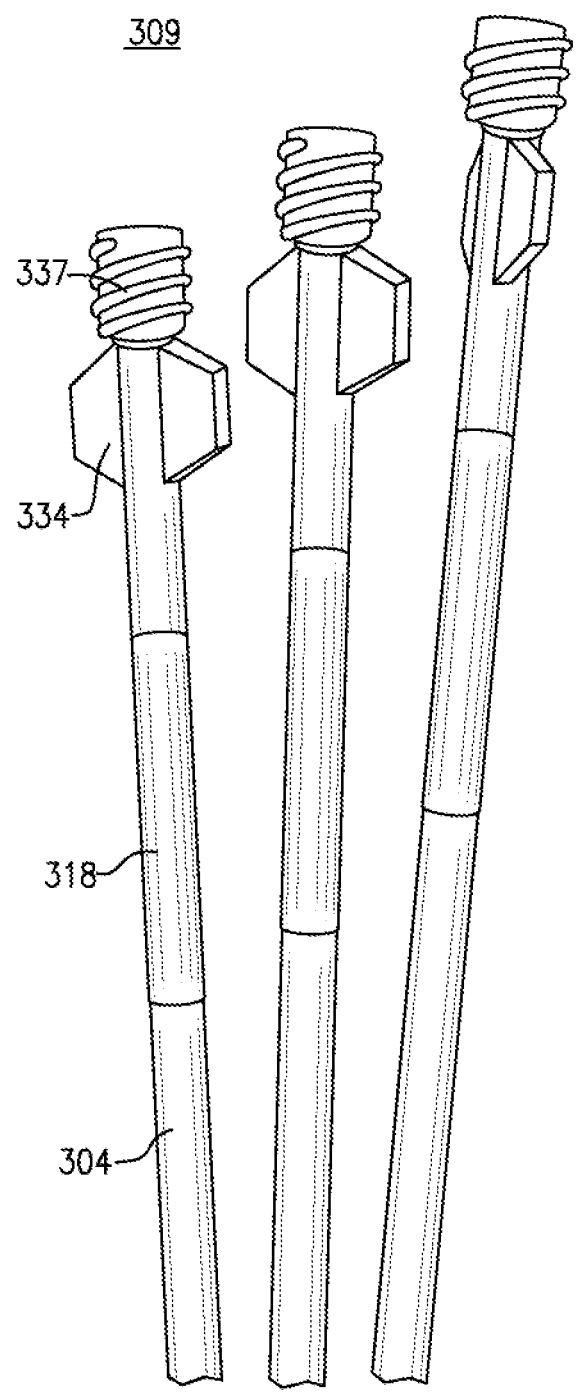
FIG. 7 is a perspective view of the opposing end of the guidewire supporting accessory of FIGS. 5 and 6.

According to this embodiment and as shown in FIG. 7, the opposing second end 309 of each hollow tubular section 304 also includes a luer hub 334 secured at one end using a section of a flexible connecting hose or tubing 318. The second luer hub 334 similarly includes a male threaded portion 337 at an opposite end. According to at least one version, the first and second luer hubs 314, 334 or part or all of the hollow tubing section 304 can be color-coded in order to distinguish the tubing section 304 and more clearly define a particular guidewire being retained by the accessory 300 that may be required during a surgical procedure.

Figure 8:
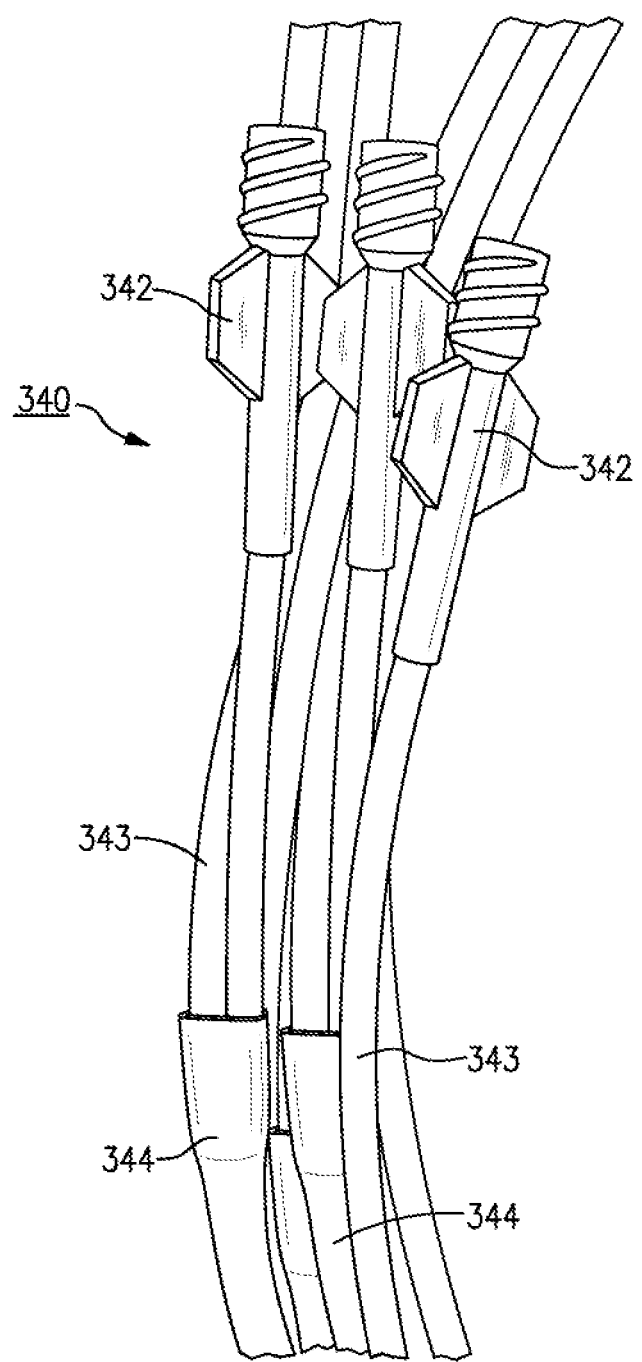
FIG. 8 is a perspective view of a side arm connector of the guidewire supporting accessory of FIGS. 5-7.
Figure 9:
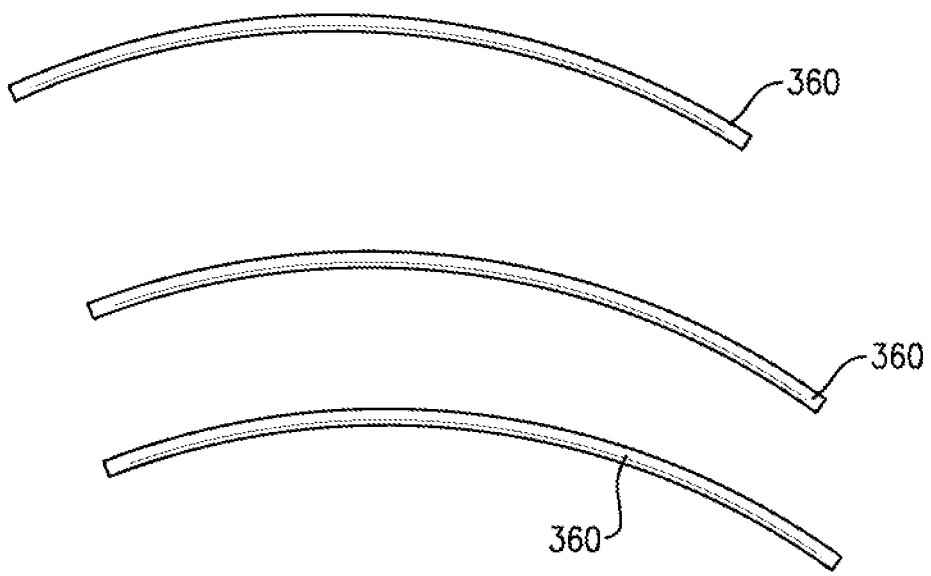
FIG. 9 is a perspective view of small section tubing that can be used in connection with the guidewire supporting accessory of FIGS. 5-8.
Figure 10:
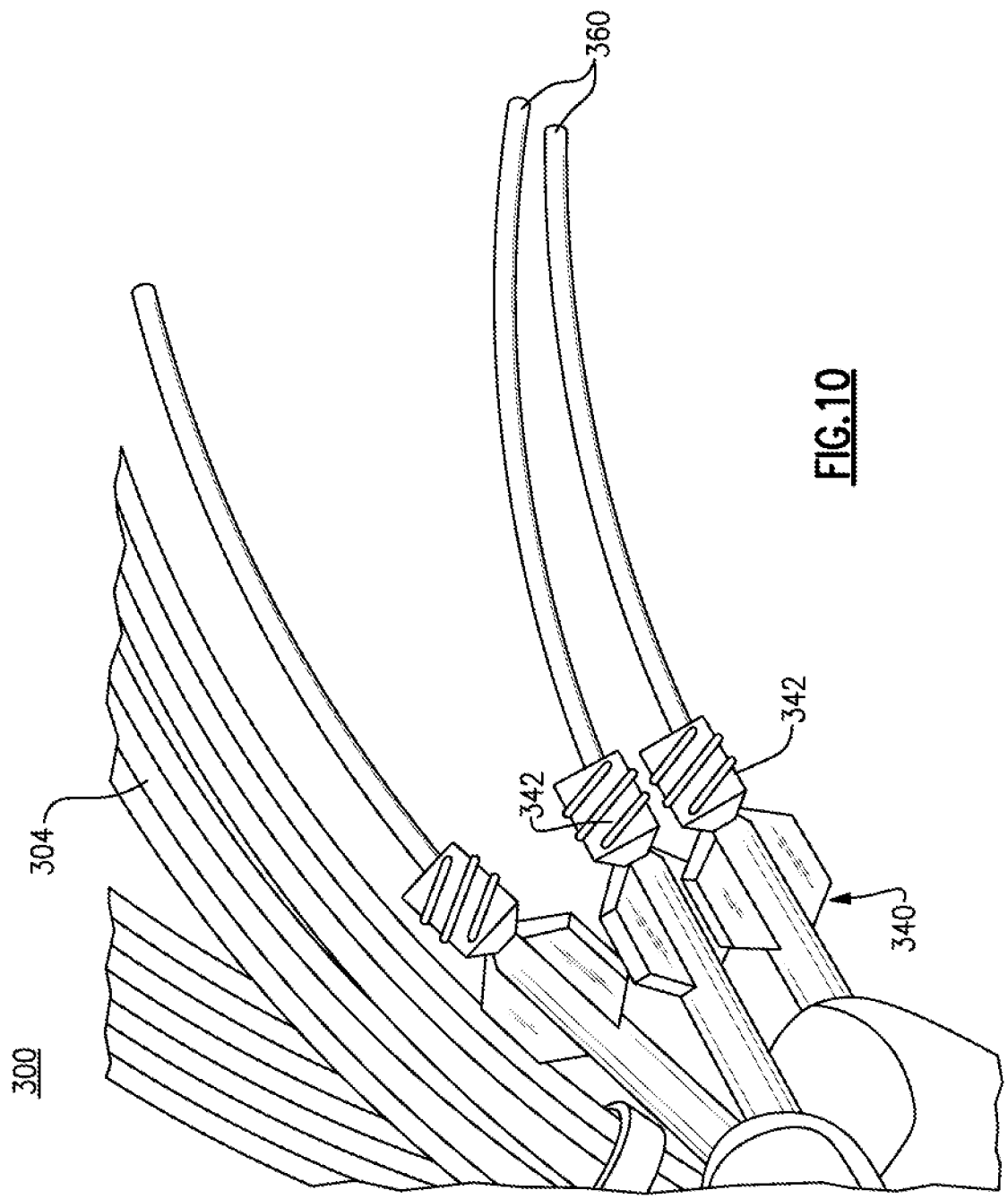
FIG. 10 is a perspective view of the small section tubing of FIG. 9, as used in the guidewire supporting accessory of FIGS. 5-8.
Figure 11:
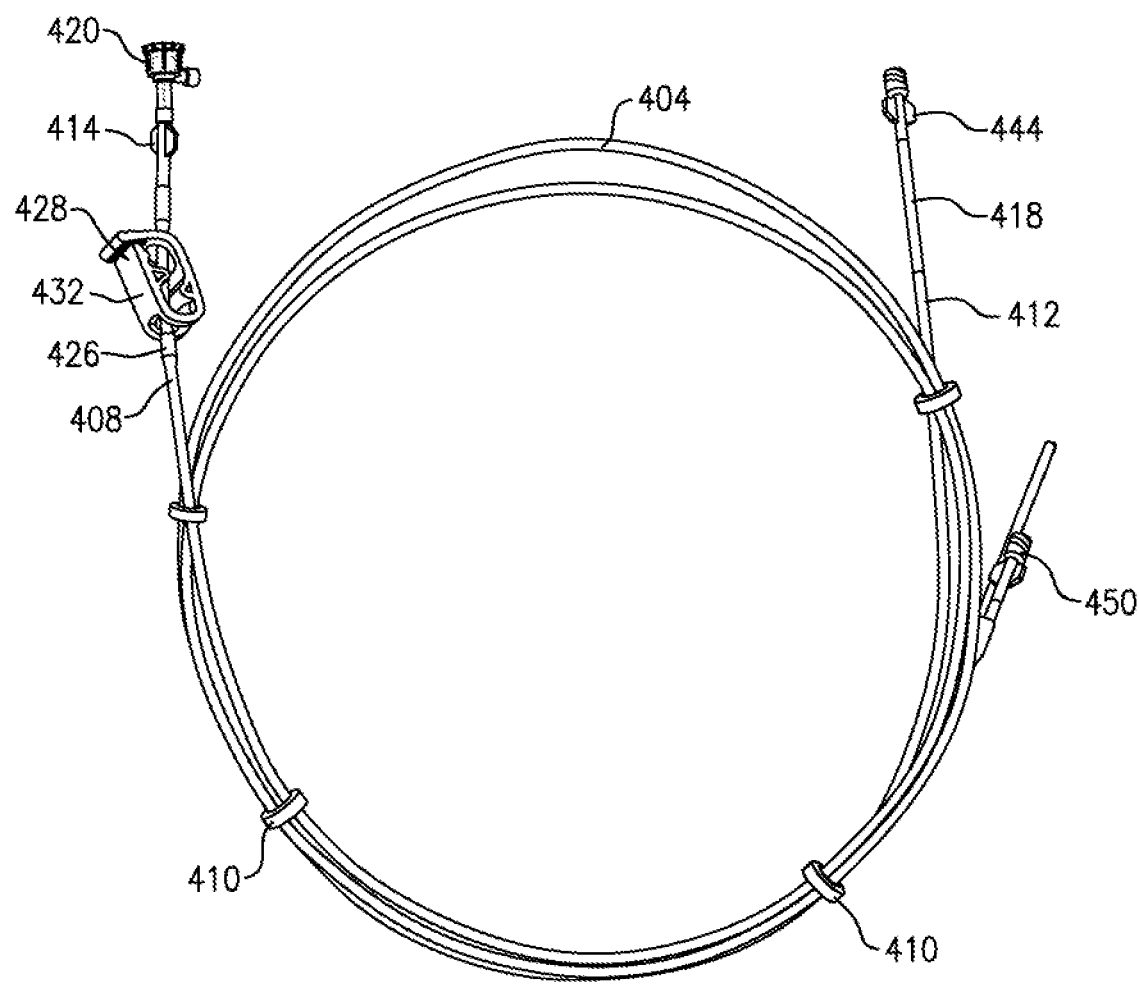
FIG. 11 is a perspective view of a guidewire supporting accessory made in accordance with another embodiment.
Figure 12:
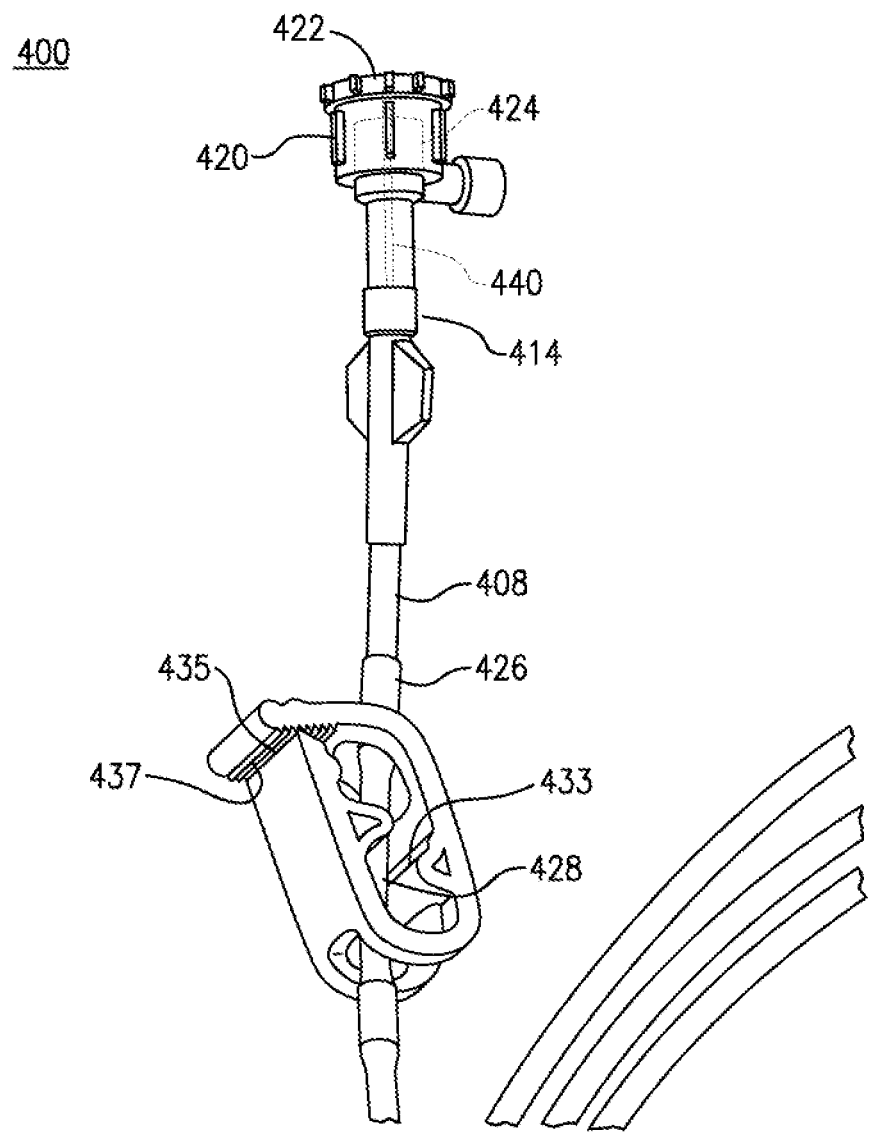
FIG. 12 is a perspective view of one end of the guidewire supporting accessory of FIG. 11.

According to this embodiment and as shown in FIG. 8, a side arm connector 340 is further disposed along an intermediate portion of at least one of the hollow tubular sections 304, which can be used to flush out the hollow tubular section 304 during insertion or removal of a guidewire. According to this embodiment, a side arm connector 340 is provided for each of the hollow tubular sections 304. Each side arm connector 340 includes a luer hub 342 that is connected to a section of hollow plastic tubing 343 extending to a side arm port 344, the latter providing access to the interior of the hollow tubing section 304. The side port connector 340 is disposed at a predetermined distance from first end 307 of the hollow tubular section 304 and the Y-connector 320. According to this embodiment, this predetermined distance is about 140 cm, although this parameter can be suitably varied, depending on the application or procedure. Among other functions that are discussed, the side arm connector 340 according to this embodiment permits flushing of a contained guidewire, as well as wetting of the wiping member 330.

According to this embodiment, a set of short tubing sections 360 will allow shorter length guidewires (not shown) to exit from the side arm channel by inserting the extra tube 360 guiding the stiff end of the wire through the side arm channel. This allows the assistant access to push the stiff end of the guidewire rather than pulling on the soft tip of the guidewire. Each of the short tubing sections 360 in this version are 10 cm pieces of 0.080" OD tubing that be inserted through the luer hub 342 and into the hollow tube section 304 via the side arm connector port 344 to engage the stiffer portion of the guidewire and permit pushability toward the first end 205 of the accessory 300. Shorter guide wires will then exit the hollow tube section 604 through the luer hub 342, allowing easier access to the stiff end of a retained guide wire.

In terms of operation, a guidewire is removed from its original package and inserted into a medical site, such as via the Seldinger technique. The original packaging is discarded. Following use, such as when a device has been implanted or located in the surgical procedure, the guidewire is removed. The guidewire is then placed within one of the hollow tubing sections 304 and the rotary valve 328 is engaged by external rotation in order to retain the guidewire in a looped configuration. The guidewire is wiped clean by the wiping member 330 and the retained guidewire can be flushed via the sidearm port 331 of the Y-connector 320 or via the sidearm connector 340.

Removal of the guidewire from the accessory 300 can be made by accessing the soft tip of the guidewire, which extends outside of the accessory 300 and pulling the guidewire from the accessory 300. Alternatively, a proximal part of the guidewire that includes the stiffer part of the guidewire may extend from the second end 309 of the hollow tubing section 304, enabling the guidewire to be pushed using a tool (not shown). According to at least one embodiment, an access port or opening can be provided in the tubing section 304 that permits access by a tool (not shown).

Alternatively, a mechanism can be provided in which a break can be provided in the tubing section enabling access to the middle stiffer part of the guide wire. A small tool/handle (not shown) can be provided to act upon and engage (push) the stiffer intermediate or proximal portion of a retained guidewire for easier access.

With reference to FIGS. 11-14, there is shown a third embodiment of a multiple guidewire retaining apparatus 400. For purposes of this description, only a single hollow tubular section 404 is shown, although it will be readily apparent that the number of tubular sections can be suitably varied as shown in the prior embodiments. The hollow tubular section 404 is retained and maintained in a coiled configuration by means of a plurality of clip members 410 that are disposed in spaced relation. The clip members 410 are examples. It will be readily apparent that other suitable means for maintaining the hollow tubular section 404 in a coiled configuration can be employed.

The hollow tubular section 404 is defined by a predetermined length (about 260 cm) and forms a coiled diameter of about 25 cm. Each of these parameters can be suitably varied. The tubular section 404 is defined by respective and opposing first and second ends 408, 412. According to this embodiment, the first end 408 includes a first luer hub 414 attached at one end to a connector 420. The connector 420 includes a screw cap 422 and a Tuohy adapter 424. The luer hub 414 is attached at an opposite end to the first end 408 of the hollow tubular section 404. A separate tubular section or sleeve 426 is provided over a portion of the hollow tubular section 404 adjacent the first end 408.

Disposed within the connector 420 is a wiping or cleaning member 440, such as a sponge ring or a section of gauze or other suitable cleaning material secured on a fitted mandrel. The wiping or cleaning member 440 is disposed to permit a retained guidewire to pass through without friction.

A hose clamp 428 is attached over the sleeve 426 adjacent the first end 404 of the hollow tubular section 404. The hose clamp 428 according to this embodiment includes a shaped body 432 having a pair of inwardly shaped clamp members 433 that are shaped and configured to engage the exterior of the sleeve 426. The relative spacing between the clamp members 433 can be varied by an a ratchet 435 at one end of the clamp body 432 configured to engage a set of spaced teeth 437 that are formed on a second end of the clamp body 432.

Figure 13:
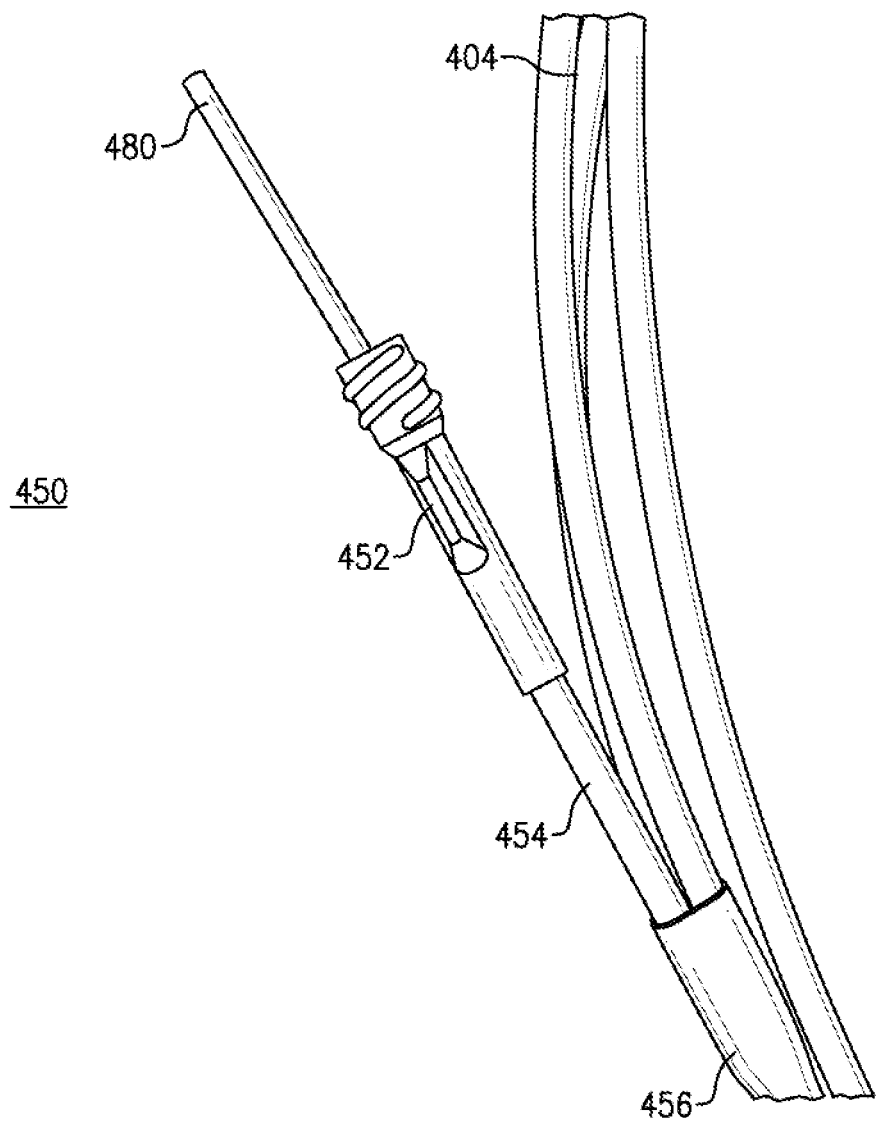
FIG. 13 is a perspective view of a side arm connector of the guidewire supporting accessory of FIGS. 11-12.

According to this embodiment, the opposite end 412 of the hollow tubular section 404 also includes a luer hub 444, the latter being attached via a connecting section of hose or tubing 418. The hollow tubular section 404 further includes a side arm connector 450 disposed intermediate to the first and second ends 408, 412. The side arm connector 450 includes a luer hub 452 having a connecting end secured to a short hollow tubular section 454 having an interior diameter equivalent to that of the hollow tubular section 404. The short hollow tubular section 454 extends to a side arm connector port 454 that splices into the hollow tubular section 404 to permit flushing of a retained guidewire, as well as the retention of shorter guidewires, as needed. The side arm connector 450 provides flushing to allow the guidewires to be wetted, which is preferable for most guidewires and required for the hydrophilic coated guidewires. As shown in FIG. 13, a short small tubing section 480 can be used in conjunction with the side arm connector 450 to engage and push the stiffer portions of retained guidewires. Additionally, the side arm connector 450 also enables the wiping member 440 to be wetted to facilitate cleaning of the retained guidewire.

Figure 14:
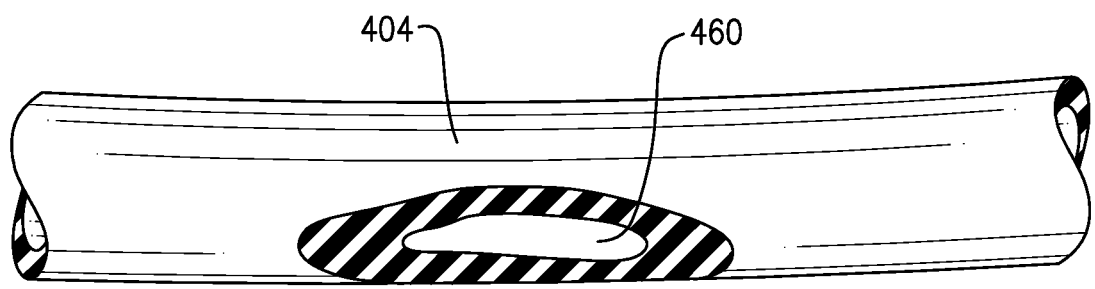
FIG. 14 is an enlarged view of a portion of a guidewire supporting accessory, including a wire access port in accordance with aspects of the invention.

As shown in FIG. 14, an intermediate portion of the hollow tubular section 404 can also include an access port 460 in addition to or as an alternative to the side arm connector port 450, FIG. 13, that enables a tool (not shown) to access the stiffer portion of a retained guidewire to enable the guidewire to be pushed through the hollow tubing section 404 and released from the accessory 400.

PARTS LIST FOR FIGS. 1-14

10 guidewire, medical
12 first or distal end, guidewire
14 floppy or soft tip, guidewire
16 second or proximal end, guidewire
18 core, guidewire
200 guidewire retaining accessory
204 hollow tubing, lengths or sections
205 first end, hollow tubular section
206 clip members
212 second end, hollow tubular section
214 luer hub
216 threaded portion, luer hub
218 connector hose or tubing
220 Y-connector
222 screw cap
224 Tuohy adapter
226 female luer connector
228 rotary valve
229 hollow (main) port, connector
231 side port
240 tapered ends, tubing sections
300 multiple guidewire retaining accessory
304 hollow tubular sections
306 clip members
307 first end, hollow tubular sections
309 second end, hollow tubular sections
314 first luer hub
317 threaded portion, first luer hub
318 connector hose or tubing
320 Y-connector
322 screw cap
324 Tuohy adapter
326 female luer connector
328 rotary valve
339 main port, connector
330 wiping or cleaning member
331 side port, connector
334 luer hub, second end
337 threaded portion
340 side arm connector
342 luer hub
343 hollow tubular section
344 sidearm connector port
360 short tubing sections
400 guidewire retaining accessory
404 hollow tubular section
408 first end, hollow tubular section
410 clip members
412 second end, hollow tubular section
414 luer hub, first
418 connecting hose or tubing
420 Y-connector
422 screw cap
424 Touhy adapter
426 sleeve
428 clamp, hose
432 clamp, shaped body
433 inwardly shaped clamp members
435 ratchet
437 teeth
440 wiping or cleaning member
444 luer hub
450 side arm connector
452 luer hub
454 short hollow tubular section
456 side arm connector port
460 access port
480 short tubing sections It will be readily apparent that the embodiment described are merely examples. Accordingly, there are a number of other variations or modifications that can be made to the guidewire retaining apparatus in accordance with the inventive concepts discussed herein and in accordance with the following claims.

The invention claimed is:

1. A guidewire support accessory comprising:
one of more hollow tubular sections maintained in a coiled configuration, each of the one or more hollow tubular sections including a first end and an opposing second end;
a connector disposed at one of the first and second ends of each hollow tubular section, the connector being sized and configured to receive a medical guidewire;
a clamp configured to individually engage and retain a guidewire within each hollow tubular section, wherein at least one of the one or more hollow tubular sections includes a side arm connector disposed intermediate the first and second ends, the side arm connector having a port extending into the tubular section and at least one short section of tubing that can be fitted within the one or more hollow tubular sections, and further including an access port provided in at least one of the one or more hollow tubular sections, the access port being disposed intermediate the first and second ends and sized to accommodate the at least one short section of tubing.

2. The guidewire support accessory as recited in claim 1, further comprising at least one wiping or cleaning member disposed within each hollow tubular section through which the medical guidewire passes when storing within the accessory and releasing the guidewire from the accessory.

3. The guidewire support accessory as recited in claim 2, in which the at least one wiping or cleaning member comprises at least one of a sponge or gauze section disposed within the accessory.

4. The guidewire support accessory as recited in claim 3, in which the at least one wiping or cleaning member is disposed within the connector.

5. The guidewire support accessory as recited in claim 1, in which the connector comprises a Y-connector having a rotary valve, wherein the rotary valve functions as the clamp.

6. The guidewire support accessory as recited in claim 1, wherein the at least one short section of tubing is configured for engagement through the port of the sidearm connector port and relative to a retained guidewire.

7. The guidewire support accessory as recited in claim 1, wherein the side arm connector enables flushing of a contained guidewire.

8. The guidewire support accessory as recited in claim 1, including at least one luer hub attached to the first end of each hollow tubular section.

9. The guidewire support accessory as recited in claim 8, in which at least one of the at least one luer hub or a portion of the one or more hollow tubular sections is color coded.

10. The guidewire support accessory as recited in claim 1, wherein the clamp is externally attached to the hollow tubular section adjacent the connector.

11. A method for manufacturing a guidewire retaining accessory, comprising:
providing one or more hollow tubular sections, each tubular section having a first end and an opposing second end;
attaching a connector to the first end of the one or more hollow tubular sections,
providing a clamp configured to retain a guidewire within the one or more hollow tubular section; and
providing a wiping or cleaning member within the accessory; and
providing a side arm connector intermediate the first and second ends and at least one short tubing section sized and configured to engage a retained guidewire.

12. The method as recited in claim 11, wherein the side arm connector is configured to flush a guidewire retained in the accessory.

13. The method as recited in claim 11, in which the clamp is disposed within the connector.

14. The method as recited in claim 13, in which the clamp is a rotary valve.

15. The method as recited in claim 11, in which the connector includes a side arm port to enable flushing of a contained guidewire.

16. The method as recited in claim 11, in which the wiping or cleaning member is disposed within the connector.

17. The method as recited in claim 16, in which the cleaning or wiping member is one of a sponge or a section of gauze.

* * * * *